(12) United States Patent (10) Patent No.: US 9,211,422 B2
Keppel et al. (45) Date of Patent: *Dec. 15, 2015

(54) ACCELERATED PARTIAL BREAST IRRADIATION WITH SHIELDED BRACHYTHERAPY APPLICATOR SYSTEM AND METHOD OF USE

(71) Applicant: Hampton University, Hampton, VA (US)

(72) Inventors: Cynthia E. Keppel, Norfolk, VA (US); Vahagn R. Nazaryan, Newport News, VA (US)

(73) Assignee: Hampton University, Hampton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/254,655

(22) Filed: Apr. 16, 2014

(65) Prior Publication Data

US 2014/0228616 A1 Aug. 14, 2014

Related U.S. Application Data

(63) Continuation of application No. 11/905,719, filed on Oct. 3, 2007, now Pat. No. 8,734,313.

(60) Provisional application No. 60/849,020, filed on Oct. 4, 2006.

(51) Int. Cl.
*A61N 5/00* (2006.01)
*A61N 5/10* (2006.01)

(52) U.S. Cl.
CPC .............. *A61N 5/1015* (2013.01); *A61N 5/103* (2013.01); *A61N 2005/1094* (2013.01)

(58) Field of Classification Search
CPC .................. A61N 5/10; A61N 5/1001; A61N 5/1003–5/1005; A61N 5/1007; A61N 5/1014–5/1017; A61N 5/1027; A61N 5/1094; A61N 5/1095; A61N 2005/1003–2005/1005; A61N 2005/1094; A61N 2005/1095; G21F 3/00

See application file for complete search history.

(56) References Cited

U.S. PATENT DOCUMENTS 6,364,823 B1 * 4/2002 Garibaldi et al. ............... 600/12
2004/0215047 A1 * 10/2004 Apple et al. ...................... 600/3

(Continued)

OTHER PUBLICATIONS

Alcón EP, EPR study of radiation stability of organic plastic scintillator for cardiovascular brachytherapy Sr90-Y90 beta dosimetry, Applied Radiation and Isotopes, Feb. 2005 pp. 301-306, vol. 62, Elsevier Ltd.

(Continued)

*Primary Examiner* — Charles A Marmor, II
*Assistant Examiner* — Carrie R Dorna
(74) *Attorney, Agent, or Firm* — Stanzione & Associates, PLLC

(57) ABSTRACT

The system and methods of the invention partially shields the radiation dose to the skin and/or other anatomical organs by using magnetically responsive material that blocks radiation, which may be fine grains of iron or other ferrous powder for example. The powder is typically injected into an IB applicator, along with inflating saline solution in case of MSB, when a skin spacing problem is encountered, or there is a risk of high doses being delivered to the critical organs surrounding a lumpectomy cavity, for example. A slight magnetic field of predetermined configuration will be applied externally to arrange the shielding material internally under the segment of surface of the IB applicator where the skin spacing is typically less than 7 mm, thereby protecting the skin from radiation damage. Monte Carlo studies to develop parameterizations for treatment planning with the IB applicator utilizing the suggested shielding material is also provided.

11 Claims, 6 Drawing Sheets

(56) References Cited

U.S. PATENT DOCUMENTS

2006/0116546 A1*  6/2006  Eng .................................. 600/3
2006/0173235 A1*  8/2006  Lim et al. ......................... 600/6

OTHER PUBLICATIONS

Beddar AS, Plastic scintillation dosimetry: optimization of light collection efficiency, Physics in Medicine and Biology, 2003, pp. 1141-1152 vol. 48 Institute of Physics Publishing, United Kingdom.

Flühs D, et al., Direct reading measurement of absorbed dose with plastic scintillators—The general concept and applications to ophthalmic plaque dosimetry American Association of Physicists in Medicine, 1996, pp. 427-434, vol. 23(3), Medical Physics, US.

Hashimoto M, Measurement of depth dose distribution using plastic scintillator, Nihon Hoshasen Gijutsu Gakkai Zasshi, Nov. 2003, pp. 1424-1431, vol. 59(11), Japan.

Abstract of Hashimoto M, Measurement of depth dose distribution using plastic scintillator, Nihon Hoshasen Gijutsu Gakkai Zasshi, Nov. 2003, pp. 1424-1431, vol. 59(11), Japan.

* cited by examiner

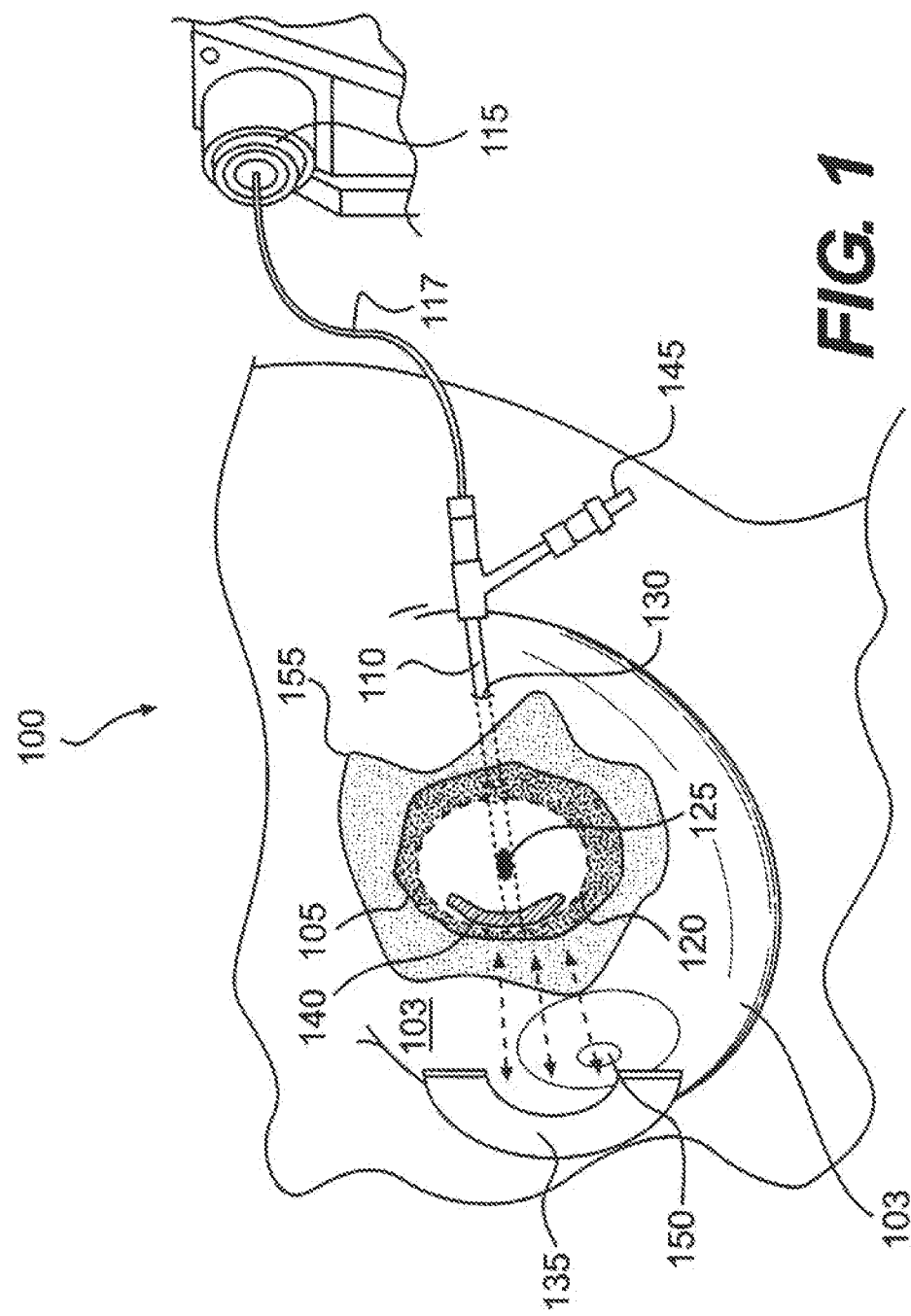

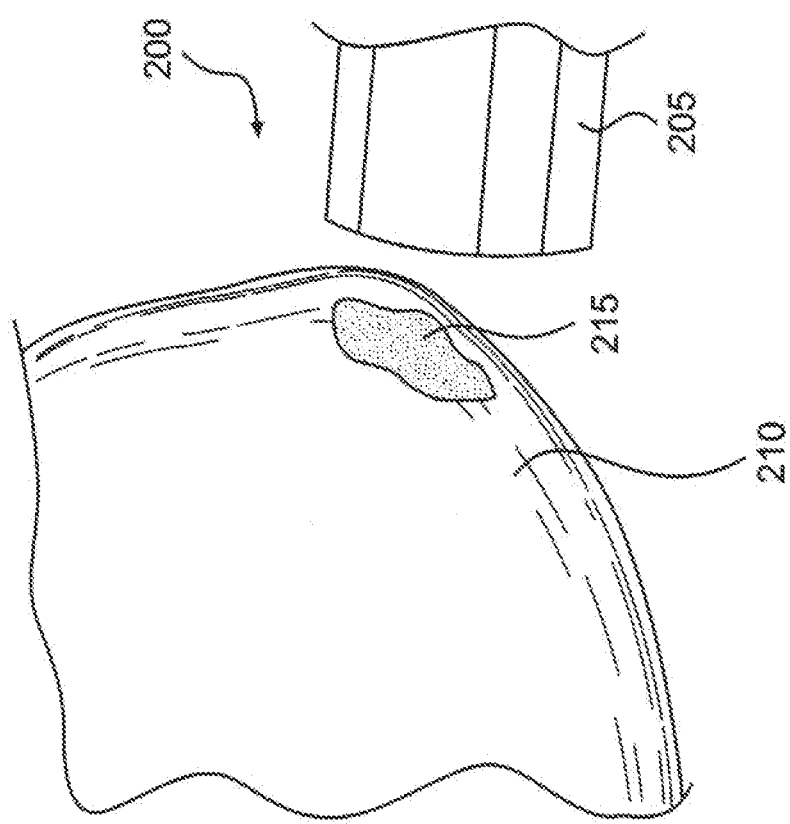

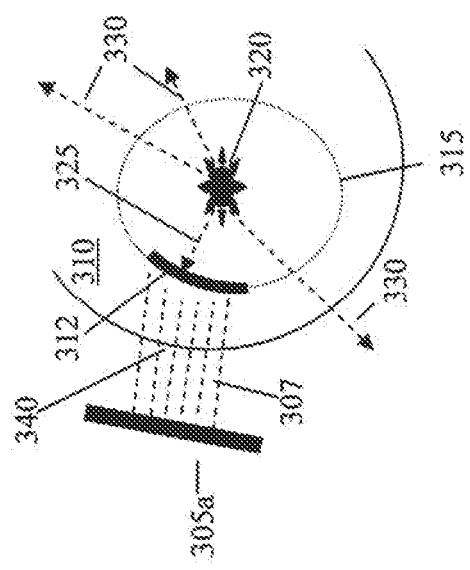
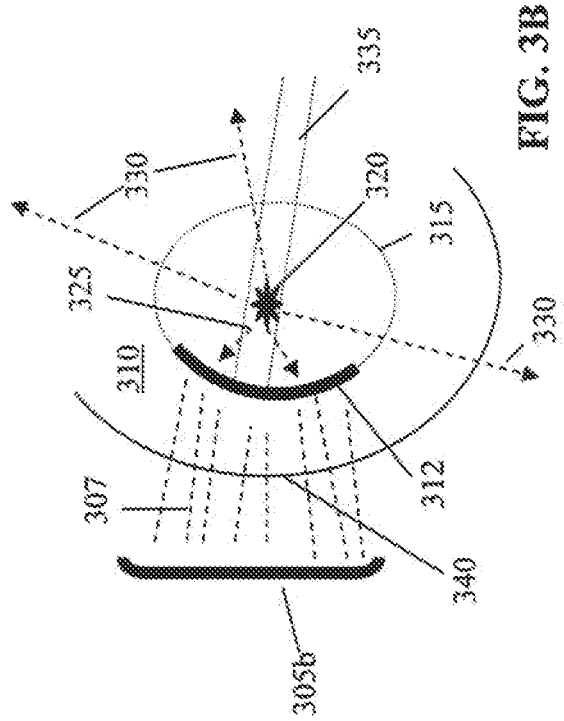
FIG. 3A
FIG. 3B

ACCELERATED PARTIAL BREAST IRRADIATION WITH SHIELDED BRACHYTHERAPY APPLICATOR SYSTEM AND METHOD OF USE

This application is a continuation application of co-pending U.S. Non-Provisional patent application Ser. No. 11/905,719 filed on Oct. 3, 2007, claims benefit of U.S. Provisional Application No. 60/849,020 filed on Oct. 4, 2006, entitled "Accelerated Partial Breast Irradiation with Shielded MammoSite Applicator and Method of Use," the disclosures of which are incorporated by reference herein in their entirety.

BACKGROUND OF THE INVENTION

1. Field of the Invention

The invention is directed to a device and method for providing radiation therapy, and more specifically, a device, system and method for providing shielded intracavitary brachytherapy (IB).

2. Related Art

For years, women with early stage breast cancers have had the option to choose breast conserving therapies (BCTs) over mastectomy. About 130,000 women are candidates for BCT in the U.S. annually. Until the mid 1990's, the only available BCT was lumpectomy, followed by external beam radiation therapy (EBRT) delivered to the whole breast in daily doses for 5-7 weeks. The combination of lumpectomy and EBRT has proven to be effective in preventing local recurrence of tumor. Despite BCT's success in fighting cancer, issues associated with scheduling 5-7 weeks of EBRT have prevented many from taking advantage of BCT. In some areas of the country, as few as 10% of medically eligible patients receive BCT. Moreover, whole breast irradiation is considered a significant contributor to adverse effects associated with this form of BCT.

Recently, methods for accelerated partial breast irradiation (APBI) have been developed, such as the technology for intracavitary brachytherapy (IB) of the breast marketed, for example, by Hologic, Inc., Cianna Medical, Xoft, Inc., and/or SenoRx, Inc. These allow patients to complete radiation treatment in 5 days. These also have better confined irradiation margins. The minimally invasive MammoSite Radiation Therapy System (MRTS) (such as marketed by Hologic, Inc.) appears to be the most widely used and fastest growing form of APBI.

MRTS works generally by implanting a small balloon into the cavity remaining after tumor removal. The balloon is inflated within the breast and then loaded with a tiny radioactive seed to deliver radiation from inside the breast directly to the tissue where cancer is most likely to recur, as well as farther from the skin where adverse reactions and cosmetic damage are dominant considerations.

If the skin-to-balloon distance is less then 7 mm, patients are not able to take advantage of MRTS. Studies show that this may affect as many as 4,000 patients each year. Small skin-to-balloon distances are associated with mild to acute adverse skin reactions, as in previous external beam therapies. These significantly impact the cosmetic outcome of BCT, which is a crucial consideration for patients undergoing breast preserving treatment.

Breast Conserving Therapy

Outcomes of multiple retrospective studies and randomized prospective trials have consistently demonstrated no significant differences between BCT and mastectomy in disease-free survival, distant disease-free survival and overall survival for an appropriately selected patient population. BCT typically involves breast-conserving surgery and radiotherapy. Until the mid 1990's the radiation therapy associated with BCT usually involved 5-7 weeks of daily treatment with external beam radiation delivered to the whole breast (during the last two-weeks of treatment a boost dose of radiation was typically delivered only to the tumor bed). The biologic argument for whole breast irradiation comes from various studies demonstrating that breast cancer is often multicentric.

Studies demonstrate that the logistic and temporal problems of scheduling 5-7 weeks of external beam radiation therapy (EBRT) have a substantial effect on patient's choice of treatment. As a result, in certain parts of the United States, as few as 10% of medically eligible patients receive BCT. Thus, even though breast-conserving surgery and EBRT have been proven to be equivalent to mastectomy in the management of women with early-stage breast carcinoma, this form of BCT has limited practicality. Additionally, it has not been definitively established how much of the clinically uninvolved breast tissue surrounding the lumpectomy cavity must be treated by radiation. Treatment of clinically uninvolved breast tissue with EBRT after lumpectomy is generally believed to play a significant role in the occurrence of acute and chronic toxicity associated with this form of BCT. Moreover, large retrospective reviews have shown that, in certain subsets of patients with early-stage breast cancer, incidence of failures outside the lumpectomy bed are rare, and the use of whole breast EBRT does not appear to significantly affect the incidence of failure outside the tumor bed.

In the face of these shortcomings of whole-breast EBRT, investigations were initiated to develop treatments that limit radiation treatment to the surgical bed plus a 10-20 mm margin of tissue circumferentially for the management of patients with early stage breast cancers who additionally satisfied certain medical eligibility criteria. Rationale for the new methodology also emphasized the delivery of larger doses of radiation per fraction to the lumpectomy cavity. This accelerated partial breast irradiation (APBI) therapy aims to preserve local control and cosmesis while decreasing the overall length of the treatment, and is typically completed for APBI in 5-7 days. The objective is to provide the breast conserving option to a larger population of women through offering a new method that is logistically simpler and more practical, and in prospective has reduced treatment related toxicities. APBI therapy addresses problems that are both side-effect and quality of life related.

Interstitial and Intracavitary APBI

Multicatheter-based interstitial brachytherapy was the focus of initial studies evaluating APBI therapy. It was used to treat the excision site plus an additional 10-20 mm margin of tissue. Follow-up data at a median of 6 years suggest that multicatheter-based APBI is comparable to whole-breast irradiation in both safety and efficacy. Despite encouraging clinical results, only a minority of institutions have adopted multicatheter-based interstitial brachytherapy. Apparently because the optimal outcome of the treatment requires extensive practitioner experience associated with both the complexity of the procedure and with the associated intricate and time-consuming treatment planning.

The MammoSite brachytherapy (MSB) applicator is one example of a new and potentially superior technology for APBI therapy, which is intended to deliver intracavitary radiation to the surgical margins after lumpectomy. The device is a double lumen balloon catheter that is surgically inserted into the tumor bed during a lumpectomy procedure or postlumpectomy during a separate open or ultrasonically guided closed procedure within ~10 weeks of the surgery.

The balloon catheter is inflated with a saline/contrast mixture to fill the entire cavity. Conformance to the surrounding tissue is checked usually with a computed tomography (CT) scan. CT images are also used to ensure an absence of air pockets between the balloon and the surrounding tissue, as well as to measure the balloon diameter, symmetry, and proximity to the skin and chest wall. The balloon catheter may be used as a high-dose rate (HDR) brachytherapy applicator to deliver intracavitary highly conformal radiation to the surgical margins plus typically an additional 10 mm of tissue surrounding the tumor bed to include clinically unapparent microscopic disease beyond the resection margins.

The MSB applicator simplifies delivery of HDR breast brachytherapy. First Phase I and II trials have already demonstrated that the device performs well clinically and provides improved dose coverage and reproducibility compared to interstitial implantation, as well as being easy to implant.

Success and Limitations of MSB

Eighty-seven institutions and 1,419 patients with stage 0, I, or II breast carcinoma who were undergoing breast conserving therapy were enrolled in a trial designed to collect data on the clinical use of the MammoSite breast brachytherapy catheter for delivering breast irradiation from May 4, 2002 through Jul. 30, 2004. The MSB device was placed in 1,403 of these patients. The MSB catheter demonstrated acceptable technical reproducibility between multiple institutions and use in appropriate groups of patients in delivering APBI. Cosmetic results at 12 months (92% good/excellent) were comparable to those reported for whole-breast radiation therapy. Early toxicity rates (infections, radiation recall) appeared acceptable. The recommended radiation dose fractionation scheme was 34 Gray (Gy) delivered at a point 10 mm from the surface of the balloon in 3.4 Gy fractions (twice daily separated by a minimum of 6 hrs) over 5 to 7 elapsed days with various commercially available, remote HDR afterloaders.

Skin Spacing—Correlation to Cosmesis:

The results of the MSB catheter trial described above confirmed previous observations that early cosmesis is related strongly to skin spacing. At 12 months, 96% of patients had a good/excellent cosmetic result with skin spacing ≥7 mm. 86% of patients with <7 mm of skin spacing had a good/excellent cosmetic result, suggesting that other factors (area/volume of tissue receiving higher doses) may impact on the ultimate cosmetic result. In 12% of patients with <7 mm of skin spacing, significant radiation effects were readily observable, and 2% had severe sequalae of breast tissue secondary to radiation effects. One of the technical eligibility criteria for participation in this trial was minimum applicator-to-skin distance of 5 mm. Explantation of the device due to inadequate balloon-to-skin distance was an overwhelming 35% of all explanted patients (3.1% overall).

Another recent study has analyzed factors associated with the cosmetic outcome achieved using the MSB applicator to treat patients with partial breast irradiation. The study population comprised 30 patients. 53.3% of the patients were reported to have an excellent cosmetic outcome and 40% had a good cosmetic outcome. The mean maximal skin doses per fraction in the excellent and good outcome groups were 354.8 cGy and 422.3 cGy, respectively. Excellent cosmetic outcome was also associated with a greater balloon-to-skin distance.

Approximately 130,000 women are candidates for BCT in the United States each year. Since the MSB treatment system's FDA approval in 2002, over 22,000 patients have been treated with this procedure. It has again been noted that the skin-balloon surface distance and balloon-cavity conformance were the main factors limiting the initial use of the MammoSite applicator. As the use of the MSB treatment system grows, it is estimated that this limitation may effect as many as 4,000 patients each year.

Radiation Recall Reactions—Skin Spacing, Chemotherapy:

Radiation recall reaction is usually broadly referring to the generalized development of a significant skin reaction (erythema, dry/moist desquamation) approximately 37 weeks after the completion of radiation therapy. Thus, both a delayed effect of radiation therapy on the skin and a redevelopment of a skin reaction secondary to the administration of radiosensitizing drugs are referred to as radiation recall reactions. It is believed that this effect is enhanced by the concurrent use of certain systemic chemotherapy agents. Adriamycin radiation recall dermatitis has been associated with external beam radiation therapy for 30 years, for example.

Development of a radiation recall reaction was evaluated in the Registry Trial on clinical use of the MSB described above, and of 442 patients that were evaluated for radiation recall reaction, 74 of these patients had received chemotherapy. A recall reaction was developed in 13.5% of patients who received chemotherapy (10 patients) versus only 1.4% (5 patients) who did not receive chemotherapy. Thus, patients who received concurrent chemotherapy were more likely to experience a recall reaction, suggesting that, in some patients, the early use of systemic chemotherapy agents can exacerbate or precipitate this reaction. Out of the 15 patients who developed a recall reaction, 3 had skin spacing <7 mm (6% of 50 patients with <7 mm skin spacing) versus 12 of 392 patients (3%) who had skin spacing >7 mm. Thus, again, patients with smaller skin spacing more frequently experienced a recall reaction (without chemotherapy).

If future studies confirm with higher certainty the association of radiation recall reaction after APBI therapy with adjuvant chemotherapy, some precautions will need to be considered. These safety measures may include 1) the delayed start of chemotherapy, 2) avoidance of certain radiosensitizing drugs, or 3) use only in patients with greater skin spacing.

Clinical Target Volume and MSB:

As already mentioned, the precise amount of clinically uninvolved tissue that must be included within the high-dose volume has not yet been definitively established. During multicatheter interstitial brachytherapy the amount of uninvolved tissue treated is an additional 10-20 mm circumferentially to the lumpectomy cavity. Three-dimensional conformal radiation therapy (3DCRT) is a relatively new and less invasive form of APBI. 3DCRT employs multiple noncoplanar beams to provide a relatively more focused dose of radiation to the excision cite plus, again, a 10-20 mm margin.

Earlier studies with the MSB applicator have included up to an additional 15 mm of tissue circumferentially. However, therapy protocols that are currently used in everyday practice include only 10 mm of clinically uninvolved tissue. Limiting factors potentially include the dose to portions of the heart and lung, but the principal dose-limiting factor for MSB is the dose to the overlying skin. Thus, a major consideration for a somewhat reduced size of the circumferentially treated tissue during MSB is not yet established clinically or scientifically, but is dictated by risk management of significant skin reactions. Yet, some studies have documented microscopic spread beyond 20 mm from the edge of the gross tumors in 29% of women with extensive intraductal component-negative breast cancers.

Improvements to the above procedures would increase overall effective treatment.

SUMMARY OF THE INVENTION

The various features of the invention improves radiation therapy overall and in certain situations, provides a simple yet effective method of minimizing these problems above, thereby both making BCT available to a larger population of women, as well as cosmetically more favorable to all, and improved radiation treatment delivery in general. In one aspect, a method partially shields the radiation dose to the skin by injecting fine grains of shielding powder into the balloon during the procedure with MRTS when a skin spacing problem is encountered. A slight external magnetic field is applied and, as the powder aligns to this field, a thin layer of radiation protection for the skin (or other tissue to be protected) will be formed. Full clinical realization is possible, including treatment planning.

In one aspect among many, the innovation to the MRTS allows more women to take advantage of APBI and therefore also of BCT. Moreover, this improved technology development facilitates better cosmetic outcome for all APBI patients, especially those also undergoing adjuvant chemotherapy.

In another aspect, a method of brachytherapy is provided. The steps include creating a radiation shield in a subject by applying a magnetic field to attract shielding material to dynamically form the radiation shield against a surface of an enclosure and applying a radiation dose wherein the radiation dose is blocked at least in part by the formed radiation shield so that radiation dose is deliverable to one area of the subject and is at least partially blocked to another area of the subject.

In yet another aspect of the invention, a method of brachytherapy is provided that includes the steps of inserting an applicator into a subject, the applicator configured to receive shielding material and a radiation source, placing the shielding material and a radiation source in the applicator and applying a magnetic field to align the shielding material along a surface of the applicator to shield a tissue area requiring protection from radiation emitted by the radiation source.

In still another aspect of the invention, a system for radiation treatment is provided that includes an applicator having a flexible containment portion configured to receive a radiation source and unformed radiation shielding material and a magnetic source configured to dynamically form a radiation shield by generating a magnetic field causing the unformed shielding material to be spatially formed by the magnetic field along a surface of the flexible containment portion, wherein radiation emitted by the radiation source is blocked in part by the formed radiation shield to protect a tissue area not under radiation treatment.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings:

FIG. 1 is a functional block diagram to illustrate a system according to principles of the invention while in use to provide shielding at a radiation treatment site;

FIG. 2 is an exemplary illustration showing how a magnetic field controls shielding material in a variable type balloon, according to principles of the invention;

FIGS. 3A and 3B are exemplary illustrations showing possible general orientation and some affects of the system of the invention;

DETAILED DESCRIPTION OF THE INVENTION

Figure 4A:
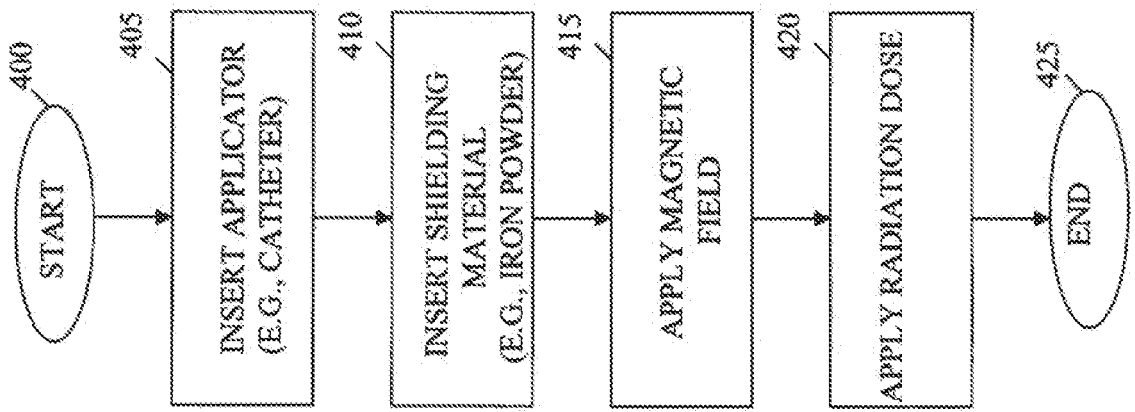
FIG. 4A is a flow diagram of an embodiment showing steps of shielding radiation at a treatment site, according to principles of the invention.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

It is understood that the invention is not limited to the particular methodology, protocols, devices, apparatus, materials, applications, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the invention.

There is a strong correlation between the cosmetic outcome of treatment of women or other subjects with early-stage breast cancer utilizing the well known MammoSite brachytherapy applicator and the spacing between the MammoSite balloon surface and the skin. Many women are not able to take advantage of MSB because of inadequate balloon-to-skin distances. Additionally, a large Registry Trial involving eighty seven institutions as well as some Phase II trials indicate that there is a definite correlation between radiation recall reactions and chemotherapy when administered within several weeks of external beam radiation therapy of the whole breast or partial breast irradiation therapy. Radiation recall reactions appeared more often if the skin dose per fraction was higher due to smaller skin spacing. Furthermore, some studies show that it may be required to increase clinical target volume margins beyond 10 mm, which is the standard in current clinical practice with MammoSite. However, the implementation of a thin, customizable, shielding layer to the MammoSite procedure significantly reduces all of these concerns, thereby facilitating increased access to the procedure, improved cosmetic outcome, and reduced radiation recall reactions.

Reference herein is made primarily in view of MRTS because of its wide spread use and the availability of clinical data. However, it should be noted that the various improvements to the method of intracavitary brachytherapy (IB) delivery are directly applicable to all of the IB treatment methods of the breast, and any other body parts where thin layer radiation shielding may be warranted. Therefore, it should be understood that other body parts of a subject (i.e., human or non-human subject) may benefit as well by the treatment technique described herein.

The various aspects of the invention provide several advantages over prior known technology including, but not limited to:

1) a practical way of reducing skin dose during the intracavitary brachytherapy of the breast via the use of shielding materials in a magnetic field for shielding part of the internal surface of the IB applicator, using optimal shielding powder configuration, material and amount. Similarly, the required electromagnetic field strength and configuration for shield shaping is provided by the invention.

2) an analytic model based on precision Monte Carlo simulations and laboratory data for determination of the required amount of powders to limit the skin dose to an optimal value deduced from several clinical trials.

3) a method and technology for application and measurement of a magnetic field which is both practical and reproducible, and provides the desired spatial distribution of shielding powders in the IB applicator.

4) a treatment planning algorithm for the IB procedure that takes as an input the analytic model and which may easily be incorporated into an existing brachytherapy treatment planning program for IB.

5) steps for implementing an entire procedure including treatment planning, powder insertion in balloon in phantom, magnetic field application external to phantom, and resulting dose measurement.

Shielded Intracavitary Brachytherapy Applicator

As described previously, prior to the invention, the risk of high doses to the skin overlying the balloon during the MSB procedure leads to a number of limitations and results in certain deficiencies associated with this treatment. It is, therefore, most desirable to mitigate such limitations by use of a technique and/or system to reduce the dose to the skin overlying and anatomical organs surrounding the IB applicator balloon while maintaining the prescribed dose to the tissue surrounding the tumor bed. A solution is provided by the methods and system of the invention, which improve cosmetic outcome after IB therapy, such as MSB therapy; reduce the risk of radiation recall reactions when patients are treated with IB and adjuvant systemic chemotherapy; allow increase in clinical target volume margins beyond 10 mm if proven necessary; and allow a larger population of women to take advantage of the breast conserving IB treatment who otherwise were ineligible due to inadequate IB applicator-to-skin distances.

FIG. 1 is a functional block diagram to illustrate a system according to principles of the invention while in use to provide shielding at a radiation treatment site, generally denoted by reference numeral 100. In the example of FIG. 1, breast 103 is representatively shown as having a treatment site 105, which might be a tumorous area within breast 103, and is shown being treated with radiation using the system 100, described below, and also is shown as having portions of breast 103 being shielded from radiation during treatment by system 100, such as the tissue near and including the areola 150 area. Breast area denoted by reference numeral 155 illustratively represents breast tissue deeper within the breast 103 which may be adjacent at least in part to the intended treatment site 105. Although shown in FIG. 1 in two dimensions for simplicity, these breast portions, i.e., treatment site 105 and tissue 155, typically involve three dimensions.

The system 100 typically includes an applicator such as catheter 110, perhaps a multilumen silicon catheter, having a radiation source pathway interiorly formed along its length with a variable inflation balloon portion 120. Further included in the system is a radiation source 125 (e.g., a $^{192}$Ir radiation seed) that might be delivered by an afterloader 115 (typically a high dose rate afterloader) having a delivery mechanism 117 to the catheter 110 for delivering a radiation dose to the treatment site 105.

FIG. 1 further illustrates that the catheter 110 with balloon portion 120 has already been advanced to the treatment site 105 through the incision 130. The balloon portion 120 is shown as having already been inflated by a solution, typically a saline solution, via fluid injection site 145. The system 100 also includes shielding material 140 and a magnet source 135 that can be applied to direct the placement and spatial orientation of the shielding material 140 within balloon portion 120. The shielding material 140 may comprise iron powder or another suitable magnetically susceptible material that provides radiation shielding ability. In the example of FIG. 1, under influence of a magnetic field, the orientation of the shielding material 140 is shown as creating a radiation shield along the inner surface of balloon portion 120 between the radiation source 125 and the skin layer proximal to the areola 150 area of the breast 103. Any tissue between the shielding material 140 (i.e., the shield) and the skin layer proximal to the areola 150 would also be shielded.

The spatial orientation of the shielding material 140 along the inner surface of the balloon portion 120 may be controlled by varying the position of the externally applied magnetic source 135 and/or varying the magnetic field intensity produced by the magnetic source 135. This varying might include changing the electromagnetic characteristics, if the magnetic source is an electromagnet; or, if the magnetic source is a permanent type magnet, changing or selecting a magnet of a particular strength, physical size and/or physical configuration.

If warranted based on a treatment plan, a broader shielding area (or, conversely, less broad shielding area) could be achieved by using more (or less) shielding material 140 and configuring the magnet 135 to spread the shielding material 140 in a broader (or less broad) configuration. Depending on the requirements of a treatment goal, a very substantial portion of the inner surface of the balloon portion 120 could be shielded as necessary with an appropriately configured and applied magnetic source 135 and adequate amount of shielding material 140. Furthermore, the magnetic field may be managed to provide a shielding area that has nearly any configuration and not simply substantially oval or substantially circular shapes, but irregular shapes as well.

The possibly fine grains of shielding material, such as iron, may be used to partially shield radiation to the skin (or other selected tissue) overlaying the IB applicator balloon, or similar applicator. Iron is used as an example material here, as it is both ferrous and a well known shield against photons for wide range of energies. Other materials, some composites, have similar properties and could be utilized equally well. These grains both respond well to applied magnetic fields and also move to a controllable configuration in the magnetic field.

The shielding material blocks radiation at least partially. In some embodiments, the shielding material may be in the form of platelets. In some instances, the shielding material may comprise magnetically susceptible steel alloy.

FIG. 2 is an exemplary illustration showing how a magnetic field controls shielding material in a variable type balloon 210, according to principles of the invention, generally denoted by reference numeral 200. Magnetic source 205 can be managed to distort the balloon 210 somewhat (but distortion of the balloon is not a necessary effect) by attraction of the shielding material 215 within the variable type balloon 210. The ex vivo exemplary balloon 210 is representative of the types of balloon characteristics and effects that could be employed with a catheter or similar applicator for in vivo applications, such as discussed previously in relation to the balloon portion 120. The spatial configuration of the shielding powder 215 is also controllable by the intensity and/or shape of the magnetic field generated by the magnetic source 205. Resulting shapes may be substantially oval, substantially circular, substantially linear, substantially rectangular, or even irregular.

In addition to iron, other shielding materials having magnetic susceptibility are possible. These might include and are not limited to gold-iron alloys with different concentrations of iron, and iron oxide nanoparticles and microparticles, for example. In these other shielding materials that may be in powder form, both reduced toxicity concerns (in case of balloon breakage) and also greater magnetic susceptibility may play a role as relevant factors when deciding on a type of shielding powder for a particular application.

FIGS. 3A and 3B are exemplary illustrations showing possible general orientation and some affects of the system of the invention. In FIG. 3A, a body part 310 is under radiation treatment. An enclosure 315 (in vivo), which might be the balloon portion of a Mammosite catheter, for example, encloses radiation shielding material 312, perhaps iron powder, for example. Within enclosure 315 a radiation source 320 is shown. A permanent magnet 305a and its magnetic field 307 (typically ex vivo) are shown attracting the radiation shielding material 312 to form a shield along the inner surface of the enclosure 315. The shield (i.e., radiation shielding material 312) is shown as blocking a portion of the radiation (denoted by reference numeral 325) while other portions of the radiation are not blocked (denoted by reference numeral 330). In this example, the skin layer and neighboring tissue (which typically includes the tissue area between the shield 312 and the magnet 305a), designated generally by reference numeral 340, are protected from the full effects of the radiation source 320, while the treatment area within body part 310 receives an intended radiation dose. The size and shape of the radiation shielding material 312 is related to the magnetic fields 307 produced by the permanent magnet 305a.

Referring now to FIG. 3B, the same situation is found as in FIG. 3A except that the magnet 305b is a controllable electromagnet (i.e., the magnetic fields are controllable) and the size of the radiation shielding material 312 along the inner surface of the balloon is larger due to a wider and perhaps stronger magnetic field 307, as compared with FIG. 3A. Also, an applicator 335 is now shown delivering the radiation source 320 to the treatment site in the body part 310 and for inflating balloon 315. Again the skin layer and neighboring tissue, designated generally by reference numeral 340, are protected from full radiation exposure emanating from radiation source 320. In both FIGS. 3A and 3B, the placement of the magnet is typically a matter of the treatment plan, usually developed at least in part using a modeling tool, discussed below.

FIG. 4A is a flow diagram of an embodiment showing steps of shielding radiation at a treatment site, according to principles of the invention, starting at step 400. The steps of FIG. 4A may be used in conjunction with the system of FIG. 1, for example. At step 405, an applicator such as a catheter is inserted into a subject for placement of the IB applicator balloon portion proximate to the treatment site. At step 410, the shielding material (such as shielding material 140) is typically injected into an IB applicator balloon, usually in those cases when a skin spacing situation is encountered. In case of the MRTS, the shielding material may be injected along with an inflating saline solution (for inflating the balloon). Prior to applying a magnetic field, the shielding powder is generally considered "unformed."

At step 415, the shielding powder may be spatially rearranged under the surface of the balloon (i.e., against the inner surface of the balloon 120) underlying the skin or overlaying an anatomical organ by application of a relatively small magnetic field external (i.e., usually, but not necessarily external) to the skin. The applied magnetic field causes the shielding powder to dynamically create an expanded shielding surface (typically a rather thin layer) based on the shape and directionality of the applied magnetic field (creating a "formed" shield). The shape of the expanded shielding surface may be varied by altering the intensity and/or directionality of the applied magnetic field. In this way a shielding "umbrella" of a size and shape appropriate to the treatment circumstance may be created by configuring the shielding powder with a desired spatial orientation, typically in opposition, at least in part, to the radiation source being applied (step 420). This "umbrella" blocks and/or reduces the radiation dose to the skin and/or any anatomical organs or tissue that may be desirable to exclude or limit from radiation treatment. The process ends at step 425.

In parallel, or typically prior to therapy, Monte Carlo simulation may be performed to determine the necessary amount of shielding powder for limiting the dose to the skin and/or anatomical organs (or tissue) not under treatment. The dose limits that result in excellent/good cosmetic outcomes can be inferred from the available clinical trial data (approx. 350-450 cGy). Different balloon-to-skin distance scenarios may also be simulated. The results of the simulation may be tested in a laboratory using breast phantoms implanted with an IB applicator. The radiation dose delivered to the surface of the breast may be verified from measurements with a detector such as a MOSFET detector, which has been proven to be a very effective radiotherapy surface dose detector. The MOSFET detector has also been tested with good results for a $^{192}$Ir source (e.g., a $^{192}$Ir radiation seed), typically employed in MSB procedures. Alternatively, an external functional imager, such as a gamma camera, can be utilized to monitor both dose and position. For position of shielding material and catheter alone, an external x-ray or CT image could be obtained. Using combined laboratory and Monte Carlo simulation data, an analytical model for surface dose calculation may be produced that is acceptable for treatment planning.

In one aspect, the model provides the required thickness of the shielding powders to achieve the desired dose limits at the skin (or other tissue) for a given skin-to-balloon distance and balloon size or geometry. It is possible to specify both skin-to-balloon distance and the skin dose limit as input parameters to the model. In another aspect, the model predicts the necessary magnetic field strength, shape and distance from the IB applicator for shielding shaping. The model includes the dependence of all of these parameters on the shielding powder's magnetic susceptibility. A range of magnetic field strengths that are adequate for a range of shielding powder layer thicknesses that are likely to be used in the clinic are determined. Magnetic field strength from the higher end of this range is typically used in practice.

Magnetic field configurations also provide optimal and reproducible shielding material spatial distributions under the surface of the IB applicator balloon. Commercially available magnetic field generators and magnetic field measurement devices may be used, perhaps customized. Electromagnets may also be used. This allows for dynamic varying of magnetic field characteristics, such as field shape, strength and distance from the IB applicator balloon. Measurement of the magnetic field(s) is practical and reproducible and provides a basis for shaping the spatial distribution of the shielding materials.

The methods and system of the invention includes providing optimal combination of magnetic field parameters and different shielding powders. Permanent magnets and electromagnets may be employed. Wide variety of customizable permanent magnets of various flexible shapes and strengths are commercially available, and may be quite suitable for controlling relevant parts of the treatment. Test results show that a relatively slight magnetic field is needed to accomplish formation of the shielding powder configuration (not much stronger than a commonly known strong "refrigerator magnet"). However, stronger magnets may be used, as appropriate.

Since CT images are typically used for treatment planning for MSB, a potential problem of CT metal artifacts from shielding powders is also addressed. An approach to reducing CT metal artifacts in intracavitary brachytherapy using acquired raw projection data, enables an algorithm that determines separate contributions from metal and non-metal objects. Images reconstructed using such algorithms contain no metal artifacts.

Figure 4B:
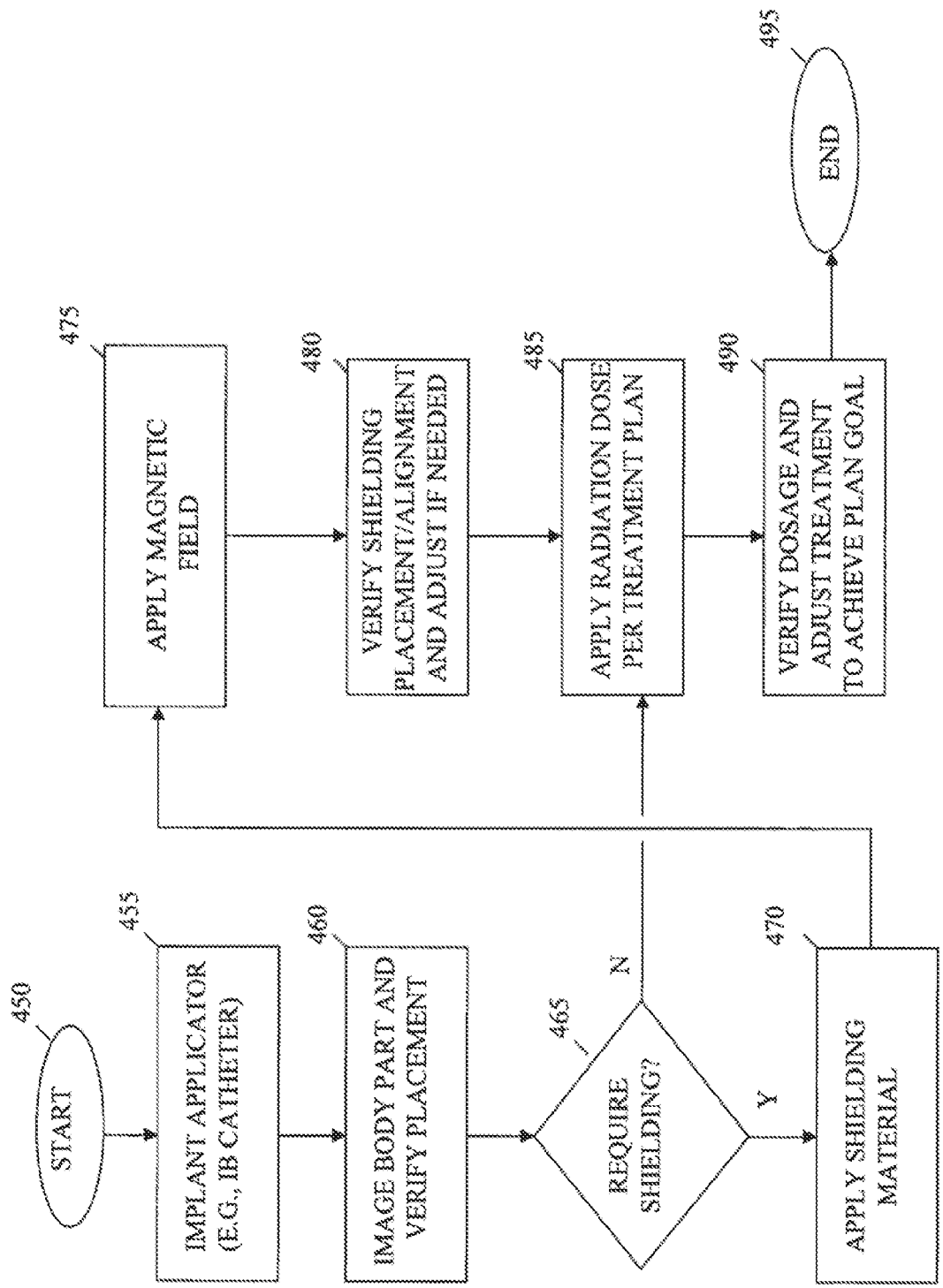
FIG. 4B is a flow diagram showing exemplary steps of an overall treatment process, according to principles of the invention.

FIG. 4B is a flow diagram showing exemplary steps of an overall treatment process, according to principles of the invention, starting at step 450. At step 455, an applicator, such as a catheter (e.g., a MammoSite catheter) may be implanted in the subject's body part and localized proximate to a treatment site for radiation therapy. The balloon portion may also be inflated. At step 460, an image may be taken of the body part to verify the actual distance and placement of the applicator balloon in relation to the treatment site and/or surface layer (e.g., skin layer) and altering, as deemed necessary. At step 465, a check is made to determine if shielding is warranted based on a predetermined distance threshold of the distance from the balloon to the surface layer and/or distance from the anticipated radiation source to the surface layer. Typically, the predetermined distance threshold is approximately 7 mm or less from the balloon to the surface layer, however, this distance threshold might vary somewhat based on specific usage. If no shielding is deemed warranted, the process continues at step 485. However, if shielding is deemed warranted, at step 470, shielding material may be applied to the applicator. At step 475, magnetic fields may be applied, typically based on results of modeling for field strength and magnetic field orientation. At step 480, the shielding material alignment and/or sizing in the applicator may be verified via imaging or dosimetric studies. At step 485, a radiation dose may be applied per a treatment plan. At step 490, the dosage may be verified (e.g., by measurement) and treatment parameters modified to achieve optimization of the dose distribution. This may include altering the magnetic field to vary the shielding effectiveness (typically by varying the spatial distribution of the magnetic material) and/or altering the position of the radiation source. This optimization may be done in real-time. At step 495, the process ends.

Figure 5:
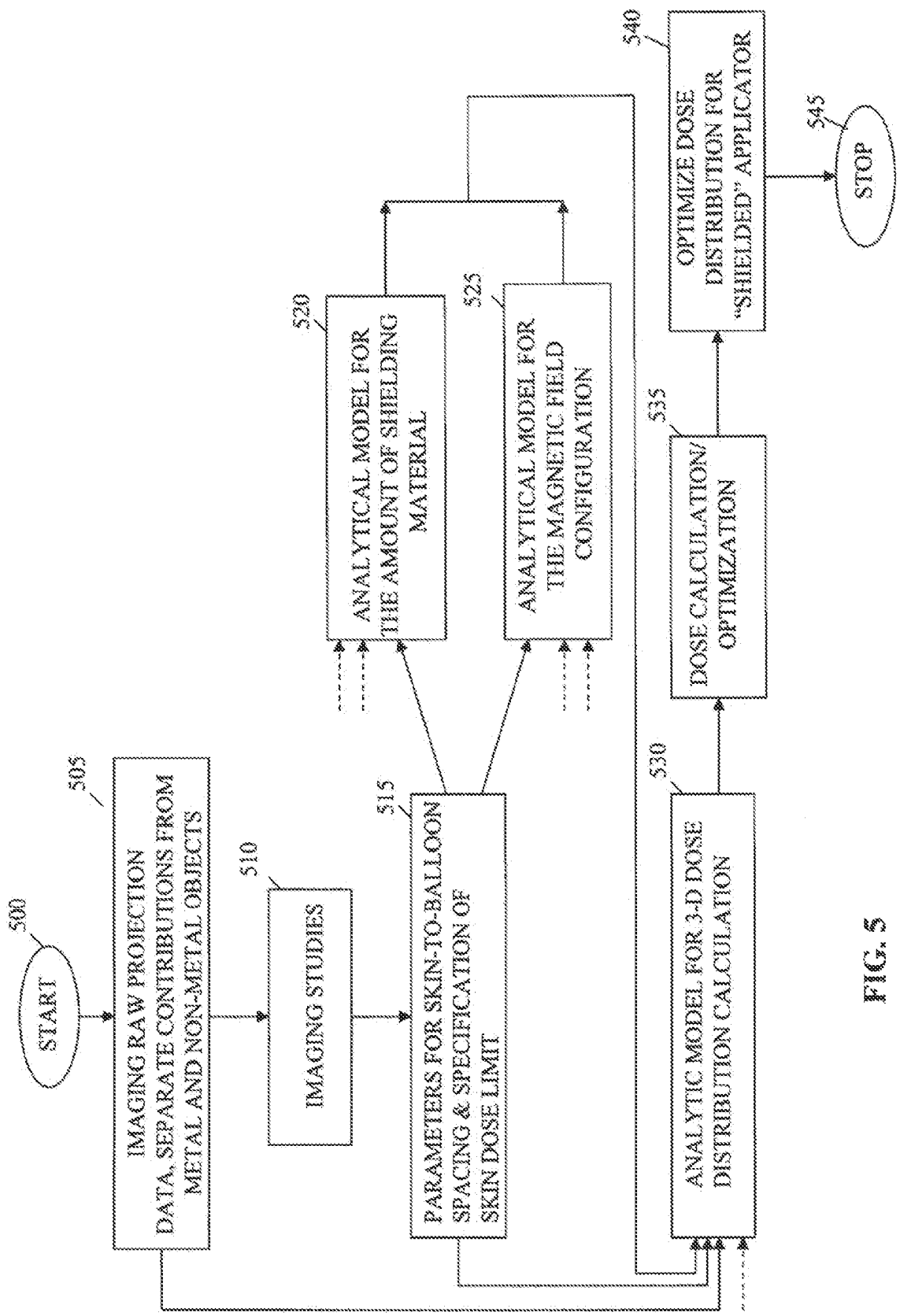
FIG. 5 is a flow diagram showing steps for modeling various factors related to the optimizing dose distribution, according to principles of the invention.

FIG. 5 is a flow diagram showing steps for modeling various factors related to the optimizing dose distribution, according to principles of the invention, starting at step 500. FIG. 5 may also be a block diagram of the components needed to execute the steps thereof. For example, the components of FIG. 5 may be executable software executing on a suitable computer platform or stored in a computer readable medium such as a memory or disk. The components of FIG. 5 may also include modeling software.

At step 505, imaging projection data studies may be performed, perhaps separating contributions from metal and non-metal objects. This may include taking an image of the body part (e.g., a breast), perhaps using Computed Tomography (CT) or another suitable imaging modality, to verify distances between the surface of the IB applicator balloon and the body part surface (step 510). At step 515, parameters for skin-to-balloon spacing and specification of skin dose limits may be established. At step 520, analytic modeling of the amount of shielding material may be produced. At step 525, analytic modeling for the magnetic field configuration may be established. This modeling may produce parameters including at least any one of: location of a magnet source; strength of the magnet source (and effective magnetic fields); and a shape of the magnetic field.

At step 530, an analytic model may be calculated using parameters from steps 515, step 520 and/or step 525 for determining a 3-D dose distribution. At step 535, the dose calculation may be optimized based on treatment goals, or other factors. At step 540, the dose distribution for the shielding applicator may be optimized to achieve an adequate dose distribution in the treatment volume with the presence of the shielding materials. This dose calculation may be performed in real-time and may provide a 3-D dose distribution in the treatment volume. If necessary, the treatment plan may be modified based on, for example, skin surface dose measurement results. In some instances, the balloon size may be adjusted by altering the amount of fluid in the balloon. This adjustment may also aid in placement of the balloon or shape of the magnetic shielding materials. At step 545, the process ends.

Outcomes

The improvements provided by the system and methods of the invention has good potential for national and international application, considering that currently more patients are choosing APBI over more conventional therapies, and even more patients and medical personnel will be able to take advantage of radiation therapy using the IB technology according to principles of the invention.

Various features provided by the invention aids in reducing risk from large radiation exposure to the skin and other anatomical organs during the IB procedure, for example for patients with less than 7 mm skin spacing. The reduction in skin's radiation exposure may in addition reduce the risk of skin reactions (such as radiation recall dermatitis) for patients also undergoing chemotherapy.

Findings using Monte Carlo simulations of the shielded intracavitary dose-delivery with MammoSite provide confidence that treatments can be carried out practically and successfully. IB employing the methods or system of the invention is more effective in maintaining high local control rates. Minimizing negative side effects is a significant benefit. The system and methods of the invention are also relatively simple to understand and use. Moreover, the methods and system of the invention may also be used in treating appropriate body parts that might benefit from thin layer shielding.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for radiation treatment, comprising:
   an applicator having a flexible containment portion configured to receive a radiation source and unformed radiation shielding material;
   a device configured to cause formation of a radiation shield by generating a magnetic field to rearrange the unformed shielding material to become spatially oriented within the flexible containment portion according to a desired spatial orientation; and
   at least one computer based component that is configured to determine a necessary amount of the shielding material for limiting the dose to tissue not under radiation treatment,
   wherein the formed radiation shield is configured to block radiation emitted by the radiation source to protect a tissue area not under radiation treatment.

2. The system of claim 1, further comprising:
   a component to determine magnetic parameters for producing the magnetic field to create the radiation shield.

3. The system of claim 1, wherein the flexible containment portion comprises a balloon portion of the applicator.

4. The system of claim 1, wherein the shielding material comprises any one of: a gold-iron alloy, iron powder, a magnetically susceptible steel alloy, and iron oxide microparticles.

5. The system of claim 1, wherein the shape of the radiation shield is alterable by altering an amount of fluid in the flexible containment portion.

6. The system of claim 1, further comprising:
   a computer executable component for modeling at least one of: an appropriate amount of shielding material for use as the radiation shield, a location of a magnetic source to produce the magnetic field, a strength of the magnetic source and a shape of the magnetic field.

7. The system of claim 1, wherein the formed radiation shield is formed along a section of a surface of the flexible containment portion while another section of the same surface remains unshielded.

8. The system of claim 1, wherein the device is configured to alter the magnetic field to vary shielding effectiveness of the radiation shield.

9. The system of claim 1, further comprising:
   a computer executable component that establishes one or more parameters for skin to the flexible containment portion spacing and skin dose limits.

10. The system of claim 9, further comprising:
    a computer executable component that calculates an analytic model based on the established one or more parameters to determine a 3-D dose distribution for a treatment plan.

11. The system of claim 10, further comprising:
    a computer based component that optimizes the 3-D dose distribution to achieve a dose distribution in a volume being treated with the presence of the radiation shield.

* * * * *